(12) United States Patent
Huang et al.

(10) Patent No.: US 11,912,972 B2
(45) Date of Patent: Feb. 27, 2024

(54) SCAFFOLD BIOREACTOR

(71) Applicant: Ark Biotech Inc., Westwood, MA (US)

(72) Inventors: Zheng Huang, Bolton, MA (US); Natalie Rose Rubio, Malden, MA (US); Orianna Elysse Kane, Boston, MA (US)

(73) Assignee: Ark Biotech Inc., Westwood, MA (US)

( * ) Notice: Subject to any disclaimer, the term of this patent is extended or adjusted under 35 U.S.C. 154(b) by 0 days.

(21) Appl. No.: 18/128,772

(22) Filed: Mar. 30, 2023

(65) Prior Publication Data

US 2023/0340388 A1    Oct. 26, 2023

Related U.S. Application Data

(60) Provisional application No. 63/334,412, filed on Apr. 25, 2022.

(51) Int. Cl.
| | |
|---|---|
| *C12M 1/12* | (2006.01) |
| *C12M 1/34* | (2006.01) |
| *C12M 1/26* | (2006.01) |
| *C12M 3/00* | (2006.01) |
| *C12M 1/00* | (2006.01) |

(52) U.S. Cl.
CPC ............ *C12M 25/14* (2013.01); *C12M 23/04* (2013.01); *C12M 23/40* (2013.01); *C12M 23/44* (2013.01); *C12M 23/48* (2013.01); *C12M 33/04* (2013.01); *C12M 41/34* (2013.01)

(58) Field of Classification Search
None
See application file for complete search history.

(56) References Cited

U.S. PATENT DOCUMENTS

| | | | | |
|---|---|---|---|---|
| 2002/0037580 | A1* | 3/2002 | Schoeb | C12M 27/20 435/293.1 |
| 2006/0223175 | A1* | 10/2006 | Hu | C12M 35/04 435/299.1 |
| 2010/0015321 | A1* | 1/2010 | Cooper-White | A61L 2/186 118/300 |
| 2010/0222771 | A1* | 9/2010 | Mitchell | B29C 48/92 606/1 |
| 2011/0262541 | A1* | 10/2011 | Lauritzen | A61K 9/0021 424/93.1 |
| 2019/0177680 | A1* | 6/2019 | Ansari | C12M 21/08 |
| 2020/0171208 | A1* | 6/2020 | Fan | A61L 27/20 |
| 2021/0145031 | A1 | 5/2021 | Leung | |
| 2022/0177823 | A1* | 6/2022 | Vila Juárez | C12M 29/14 |
| 2022/0195359 | A1* | 6/2022 | Lavon | C12M 41/26 |

FOREIGN PATENT DOCUMENTS

| | | | | |
|---|---|---|---|---|
| WO | WO-2020222239 | A1 * | 11/2020 | A23L 13/00 |
| WO | 2022038240 | | 2/2022 | |

OTHER PUBLICATIONS

Chen et al., A Novel Rotating-Shaft Bioreactor for Two-Phase Cultivation of Tissue-Engineered Cartilage, 2004, Biotechnol. Prog., 20, pp. 1802-1809 (Year: 2004).*

(Continued)

*Primary Examiner* — Holly Kipouros
(74) *Attorney, Agent, or Firm* — Van Pelt, Yi & James LLP

(57) ABSTRACT

A system for culturing cells includes a bioreactor including a scaffold on which the cells tend to adhere. The system further includes a circulatory system that intermittently flows fluid over the scaffold.

17 Claims, 16 Drawing Sheets

(56) References Cited

OTHER PUBLICATIONS

Hayashi et al., Impacts of channel direction on bone tissue engineering in 3D-printed carbonate apatite scaffolds, 2021, Materials and Design, 204, 109686 (Year: 2021).*
Stokols et al., Freeze-dried agarose scaffolds with uniaxial channels stimulate and guide linear axonal growth following spinal cord injury, 2006, Biomaterials, 27, pp. 443-451 (Year: 2006).*
Forcier et al., Farm in a Lab: Cultivating A Lab-Grown Meat Solution, 2020, Worcester Polytechnic Institute. (Year: 2020).*
Nankervis et al., Optimizing T Cell Expansion in a Hollow-Fiber Bioreactor, Current Stem Cell Reports, 2018, pp. 46-51.

* cited by examiner

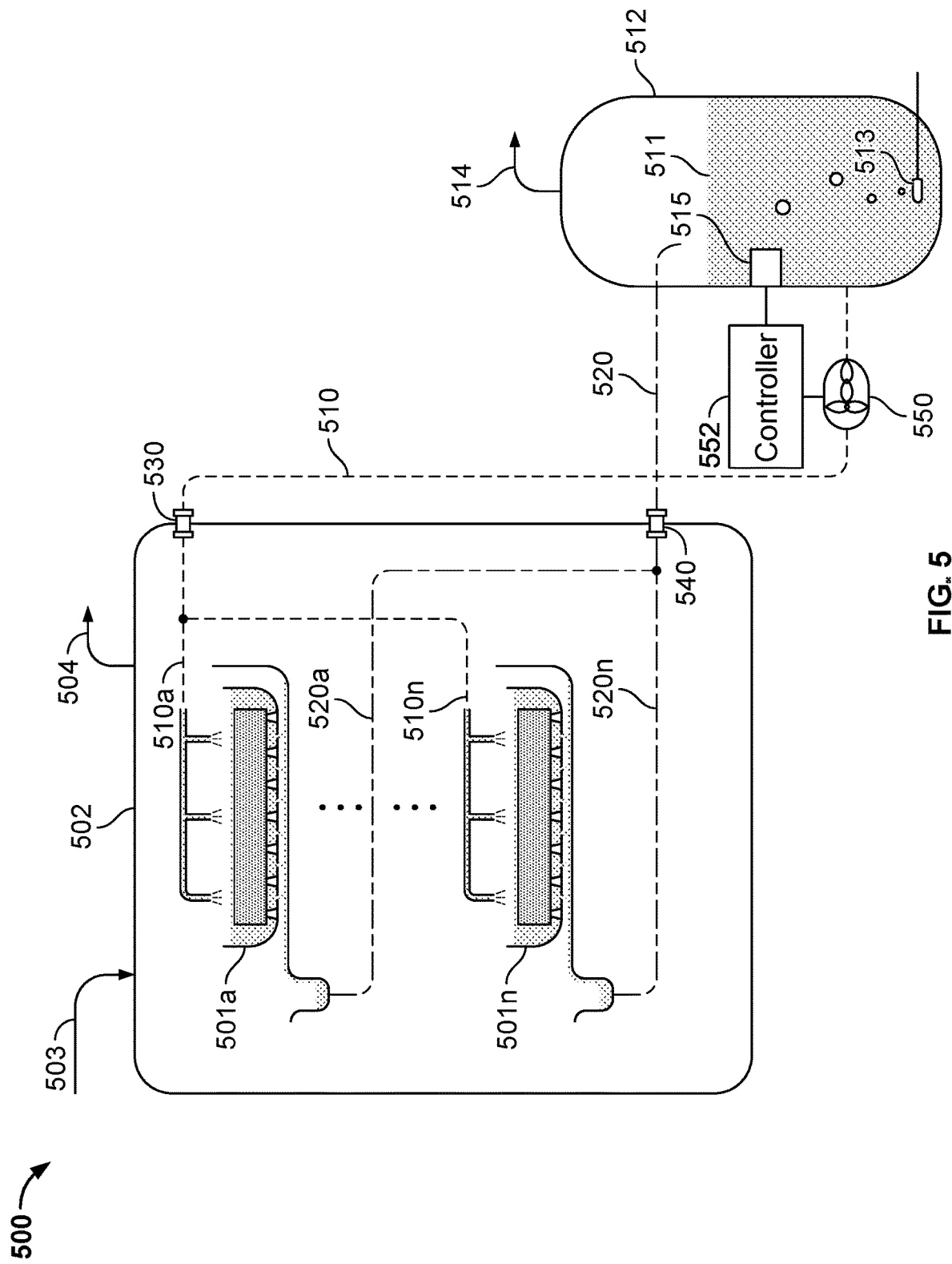

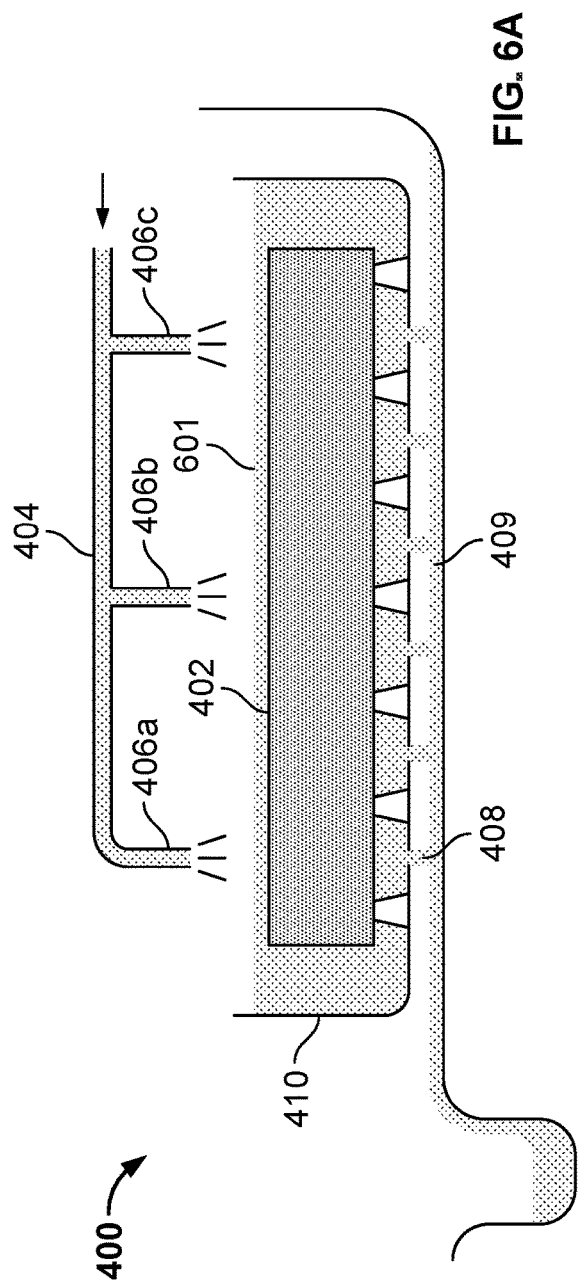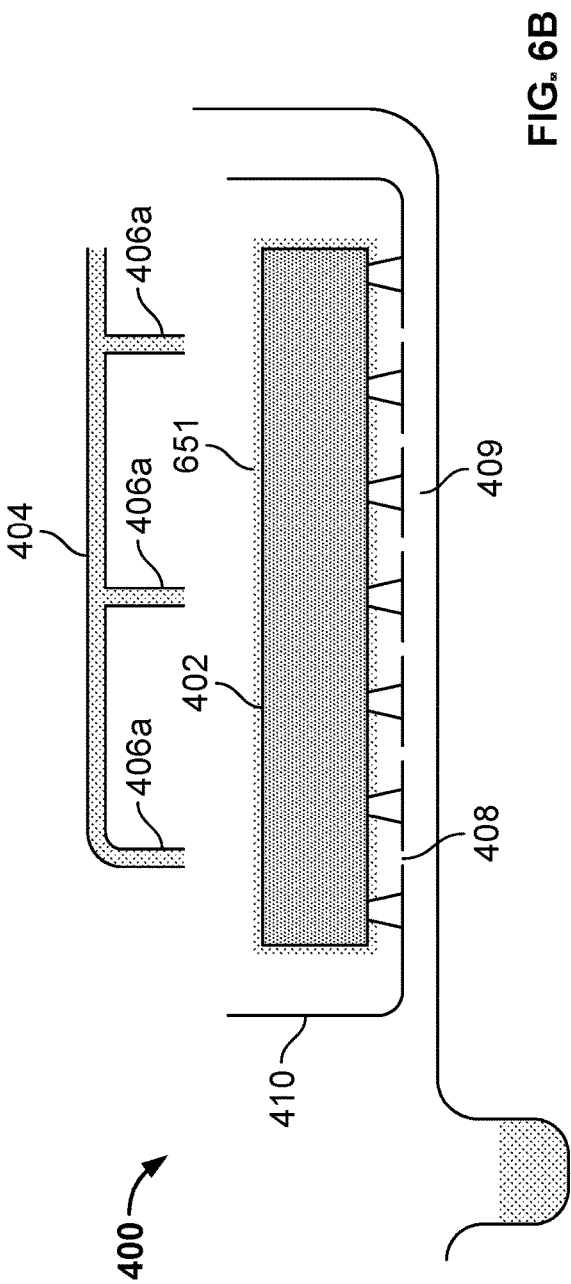

SCAFFOLD BIOREACTOR

CROSS REFERENCE TO OTHER APPLICATIONS

This application claims priority to U.S. Provisional Patent Application No. 63/334,412 entitled SCAFFOLD BIOREACTOR filed Apr. 25, 2022 which is incorporated herein by reference for all purposes.

BACKGROUND OF THE INVENTION

To produce structured (i.e., whole-cut) cultivated meat products, cells are proliferated and/or differentiated on scaffolding substrates to produce tissues of targeted composition, structure, density, size, texture, and shape. Established large-scale bioreactors (e.g., agitated vessels) are not suitable to support whole-cut meat production due to challenges associated with cultures that necessitate multiple cell types, differentiation processes, scaffold integration, macro-scale structures, and/or high tissue density. For example, existing systems may use stirred tanks to produce unstructured meat. Unstructured meat may be produced by proliferating animal cells within stirred tanks. However, the method of agitation in stirred tanks prevents structured tissue formation for whole-cut meat production. Other established bioreactor systems may be suitable to support whole-cut meat production, but they are not large-scale or cost-effective. For example, hollow fiber bioreactors may be used to produce structured tissue for whole-cut meat production. However, hollow fiber bioreactors are expensive to operate and have not been scaled-up to industrial production volumes. Large-scale production of whole-cut meat will require new bioreactor systems that enable the above properties while remaining scalable and low-cost and integrating with upstream and downstream unit operations.

BRIEF DESCRIPTION OF THE DRAWINGS

Various embodiments of the invention are disclosed in the following detailed description and the accompanying drawings.

FIG. 5 is a diagram illustrating a scaffold bioreactor in accordance with some embodiments.

FIGS. 6A and 6B illustrate an operation of a scaffold bioreactor in accordance with some embodiments.

DETAILED DESCRIPTION

Figure 1:
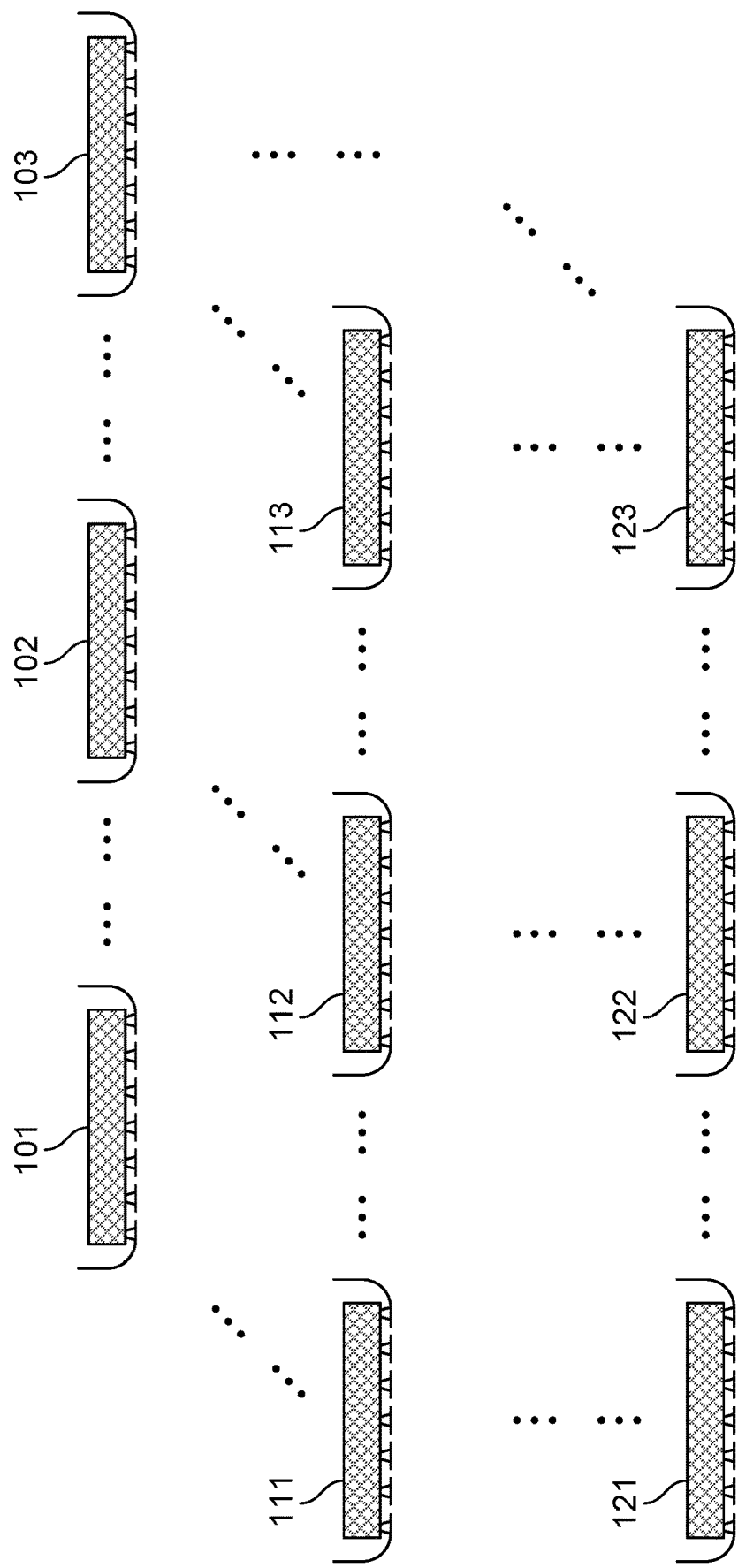
FIG. 1 is a diagram illustrating a three-dimensional layout of scaffold trays in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

There are several technical challenges that need to be overcome for large-scale product of structured cultivated meat products. These challenges may include, but are not limited to tissue thickness, density, structure and texture, cell inoculation, and/or medium conservation.

Thickness: Creating a thick end product with a scaffold-based approach gives rise to issues with cell infiltration and nutrient and oxygen diffusion. Also, there should be consideration of the ratio of scaffold material to biomass, depending on the quality requirements of the end-product.

Density: The scaffold design will dictate the thickness of the construct while the cell inoculation density, distribution, proliferation and differentiation will dictate the density of the construct. At low vs. high cell densities, the nutrient and oxygen demands will differ. At high cell densities, achieving sufficient oxygenation in the bulk of the scaffold will be a challenge. Scaffold compaction by differentiating muscle fibers may also present issues.

Structure & Texture: The defining characteristic of whole-cut meat is structure which informs texture. Muscle fibers should be macroscopically aligned, thick and long. The scaffold structure will largely dictate cell alignment. The other element of structure is fat marbling.

Inoculation: Seeding scaffolds with cells is a challenge because the cells should adhere to the scaffold and not the bioreactor vessel itself. Additionally, inducing cell infiltration in thick scaffolds is difficult, as they tend to localize on the surfaces of scaffolds rather than migrate through the bulk of the material.

Medium Conservation: Culture media is a leading cost contributor to cultured meat production. Media should be conserved wherever possible to decrease operating costs. Specifically, high value ingredients should be used efficiently and recycled if possible.

A scaffold bioreactor that allows high volume production of whole-cut meat for the cultivated meat industry is disclosed herein. The scaffold bioreactor is designed to support cell proliferation and/or differentiation of cultured cell types (e.g., mammalian, avian, fish, reptile, crustacean, molluscan, insect) to produce thick, dense and/or structured tissues while balancing efficient nutrient and oxygen delivery and waste removal. The scaffold bioreactor may include a vessel, an array of scaffold trays, a recirculation media tank, and a series of circulation manifolds. As seen in FIG. 1, an array of scaffold trays 101, 102, 103, 111, 112, 113, 121, 122, 123 may be arranged in a three-dimensional layout 100 within a rectangular or other shape vessel (e.g., cylindrical, square, pentagon, hexagon, etc.). The interior of the scaffold bioreactor does not require any moving parts which maximizes space utilization and reduces production costs while ensuring the vessel is easy to clean and sterilize. The design can be scaled to different sizes to better meet user requirements during process development, pilot, and industrial operations. It helps reduce scale-up risk and accelerate the industrialization of whole-cut cultivated meat.

The scaffold trays 101, 102, 103, 111, 112, 113, 121, 122, 123 are integrated with a dispensing manifold that provides fluid (e.g., cell inoculum, growth media, differentiation media, concentrated feeds, acid/base solutions, wash buffers, cleaning solutions, etc.) into a corresponding scaffold tray that may or may not contain a scaffold. In some embodiments, a scaffold tray is stationary. In some embodiments, a scaffold tray is rotating. In some embodiments, a scaffold tray is mobile.

Figure 2:
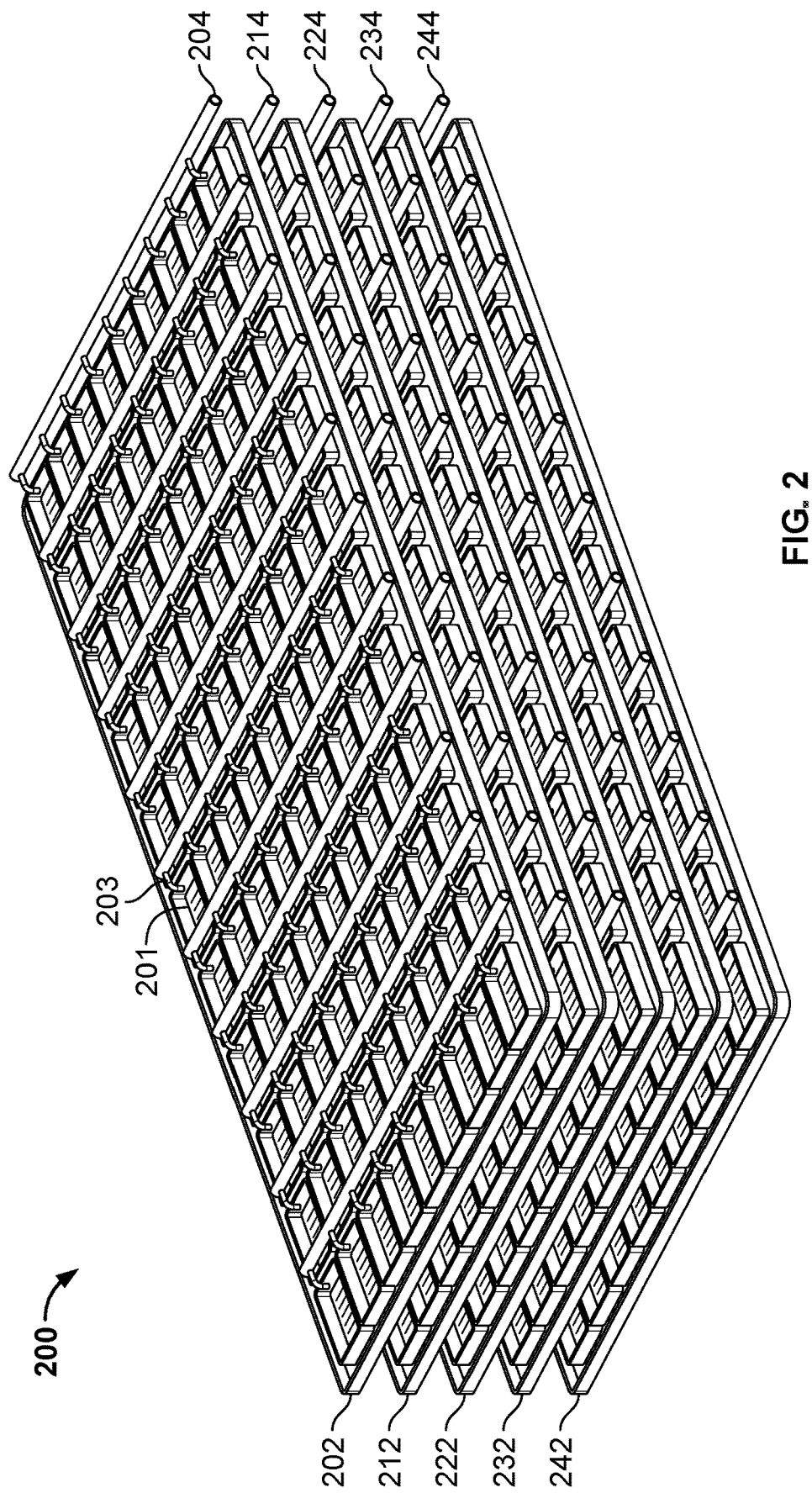
FIG. 2 is a diagram illustrating layers of scaffold tray arrays in accordance with some embodiments.

A scaffold bioreactor may include a plurality of layers of scaffolds or scaffold tray arrays. As seen in FIG. 2, the scaffold bioreactor 200 is comprised of a first array of scaffold trays 202, a second array of scaffold trays 212, a third array of scaffold trays 222, a fourth array of scaffold trays 232, and a fifth array of scaffold trays 242. Each of the rows in a scaffold tray is associated with a corresponding row manifold. For example, a first row of scaffold tray 202 is associated with row manifold 204, a first row of scaffold tray 212 is associated with row manifold 214, a first row of scaffold tray 222 is associated with row manifold 224, a first row of scaffold tray 232 is associated with row manifold 234, and a first row of scaffold tray 242 is associated with row manifold 244. Each tray, such as tray 201, is associated with one or more corresponding dispensing manifolds, such as dispensing manifold 203.

Figure 3:
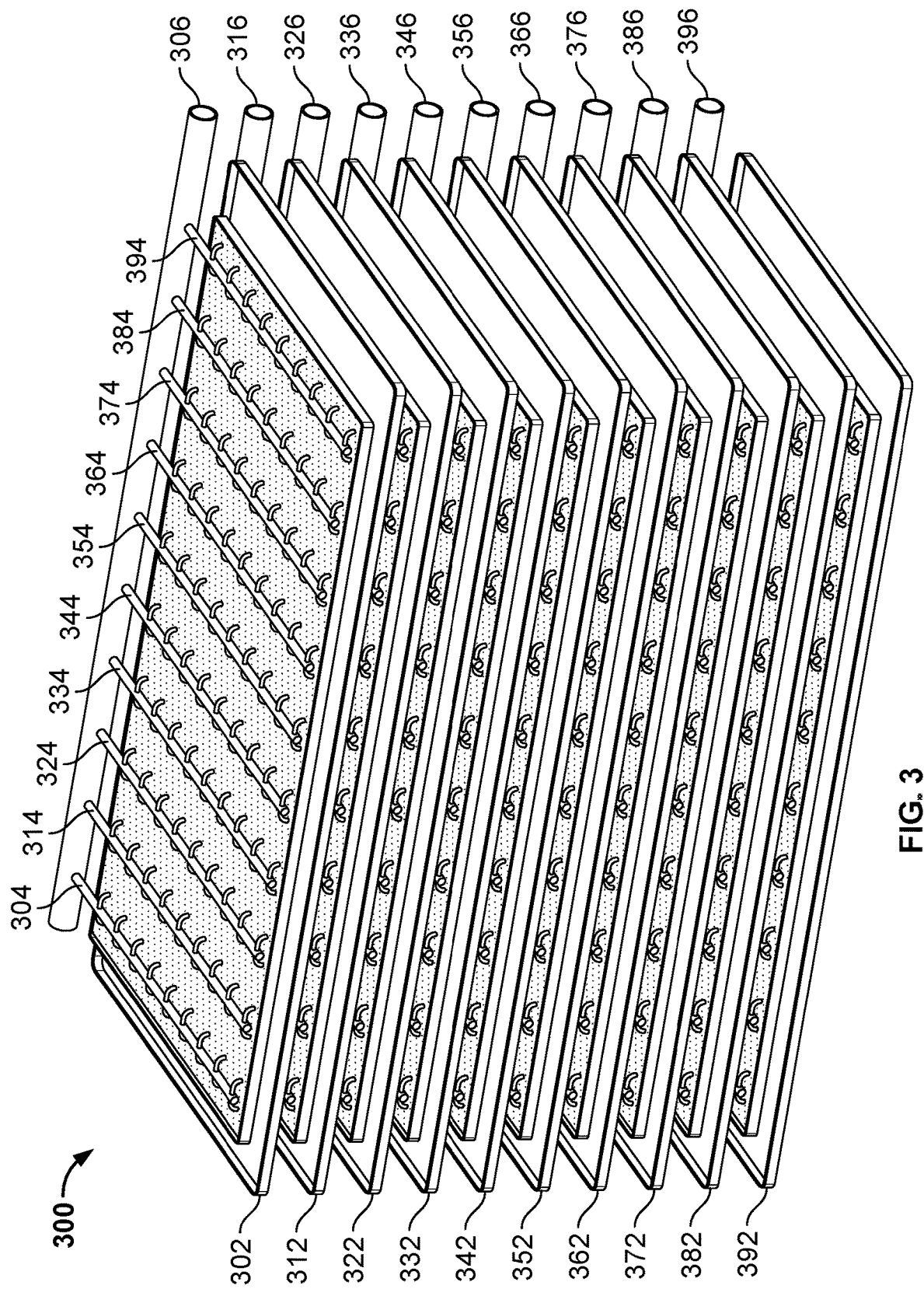
FIG. 3 is a diagram illustrating layers of scaffold tray arrays in accordance with some embodiments.

A scaffold bioreactor may include a central manifold that is coupled to each of the row manifolds associated with a scaffold tray array. As seen in FIG. 3, scaffold bioreactor 300 is comprised of a first array of scaffold trays 302, a second array of scaffold trays 312, a third array of scaffold trays 322, a fourth array of scaffold trays 332, a fifth array of scaffold trays 342, a sixth array of scaffold trays 352, a seventh array of scaffold trays 362, an eight array of scaffold trays 372, a ninth array of scaffold trays 382, and a tenth array of scaffold trays 392. Each scaffold tray is associated with a corresponding central manifold. For example, the first array of scaffold trays 302 is associated with a first central manifold 306, the second array of scaffold trays 312 is associated with a second central manifold 316, the third array of scaffold trays 322 is associated with a third central manifold 326, the fourth array of scaffold trays 332 is associated with a fourth central manifold 336, the fifth array of scaffold trays 342 is associated with a fifth central manifold 346, the sixth array of scaffold trays 352 is associated with a sixth central manifold 356, the seventh array of scaffold trays 362 is associated with a seventh central manifold 366, the eighth array of scaffold trays 372 is associated with an eighth central manifold 376, the ninth array of scaffold trays 382 is associated with a ninth central manifold 386, and the tenth array of scaffold trays 392 is associated with a tenth central manifold 396. Each central manifold is associated with a plurality of row manifolds. For example, central manifold 306 is associated with row manifolds 304, 314, 324, 334, 344, 354, 364, 374, 384, 394.

A manifold is configured to maintain an aseptic environment, provide temperature control, facilitate culture medium recirculation and oxygenation, and acquire data on system productivity. Fluid provided by a manifold is either retained in the trays or drained from the trays. When fluid is drained from the trays, it may be channeled to a media recirculation tank for online analysis, adjustment of pH, addition of nutrients or other factors, additional oxygenation, and/or for disposal. Media is recirculated from the media recirculation tank to the scaffold bioreactor via the manifolds.

Figure 4:
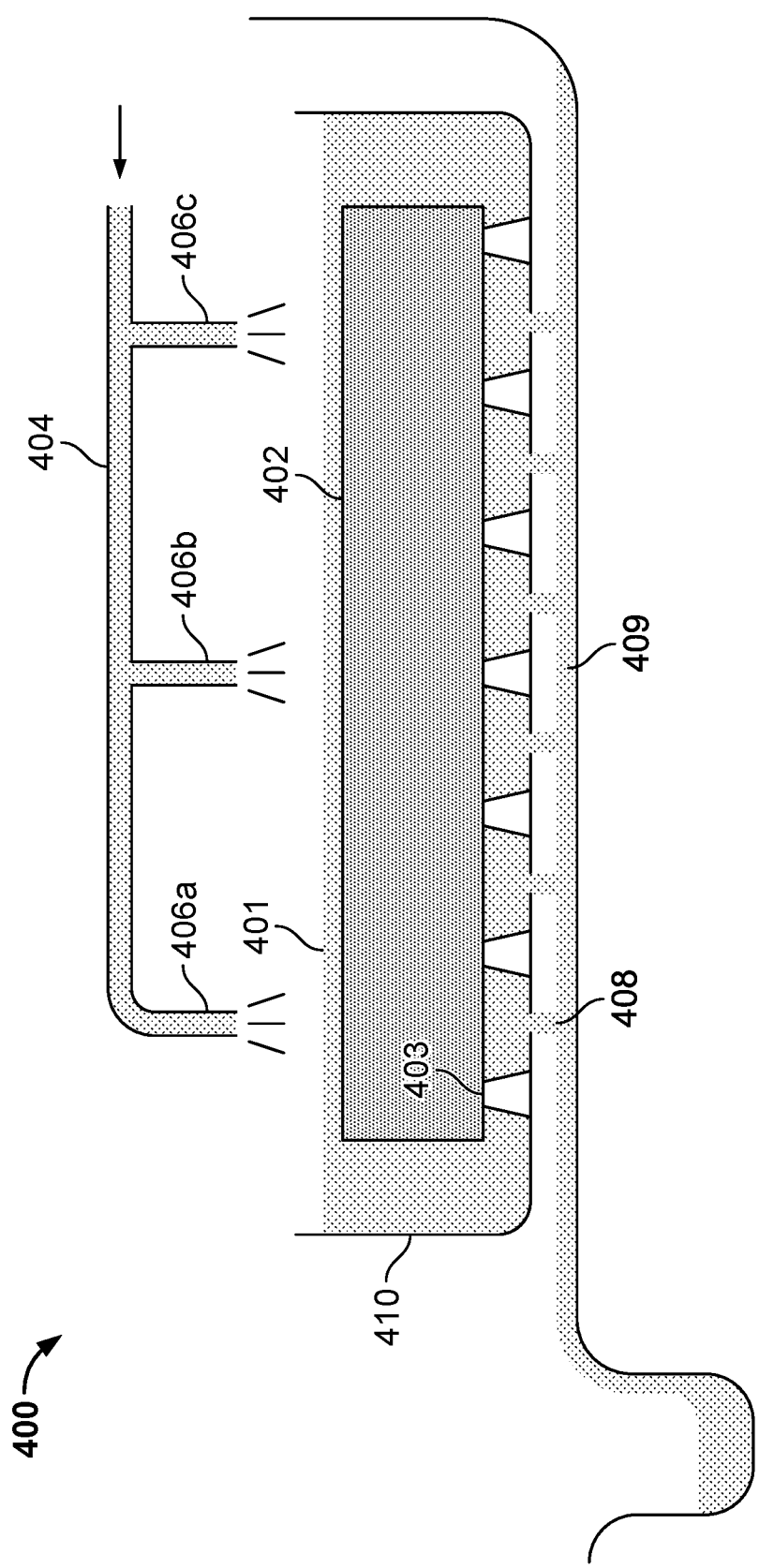
FIG. 4 is a diagram illustrating a scaffold tray in a scaffold bioreactor in accordance with some embodiments.

FIG. 4 is a diagram illustrating a scaffold tray in a scaffold bioreactor in accordance with some embodiments. In some embodiments, a scaffold bioreactor includes a single scaffold tray. In some embodiments, a scaffold bioreactor includes a plurality of scaffold trays.

Figure 15:
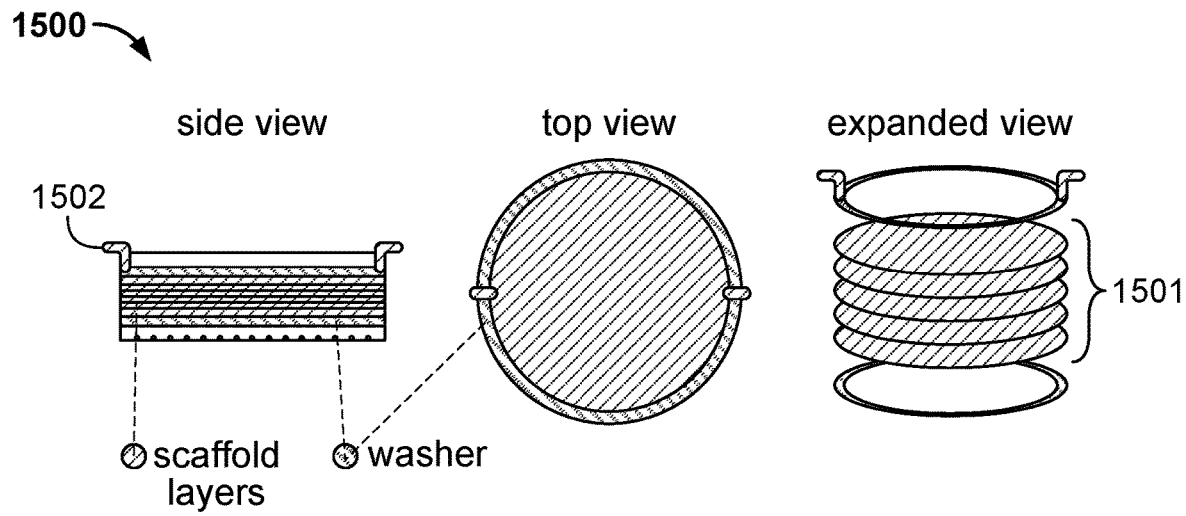
FIG. 15 illustrates an example of a scaffold tray in accordance with some embodiments.
Figure 16:
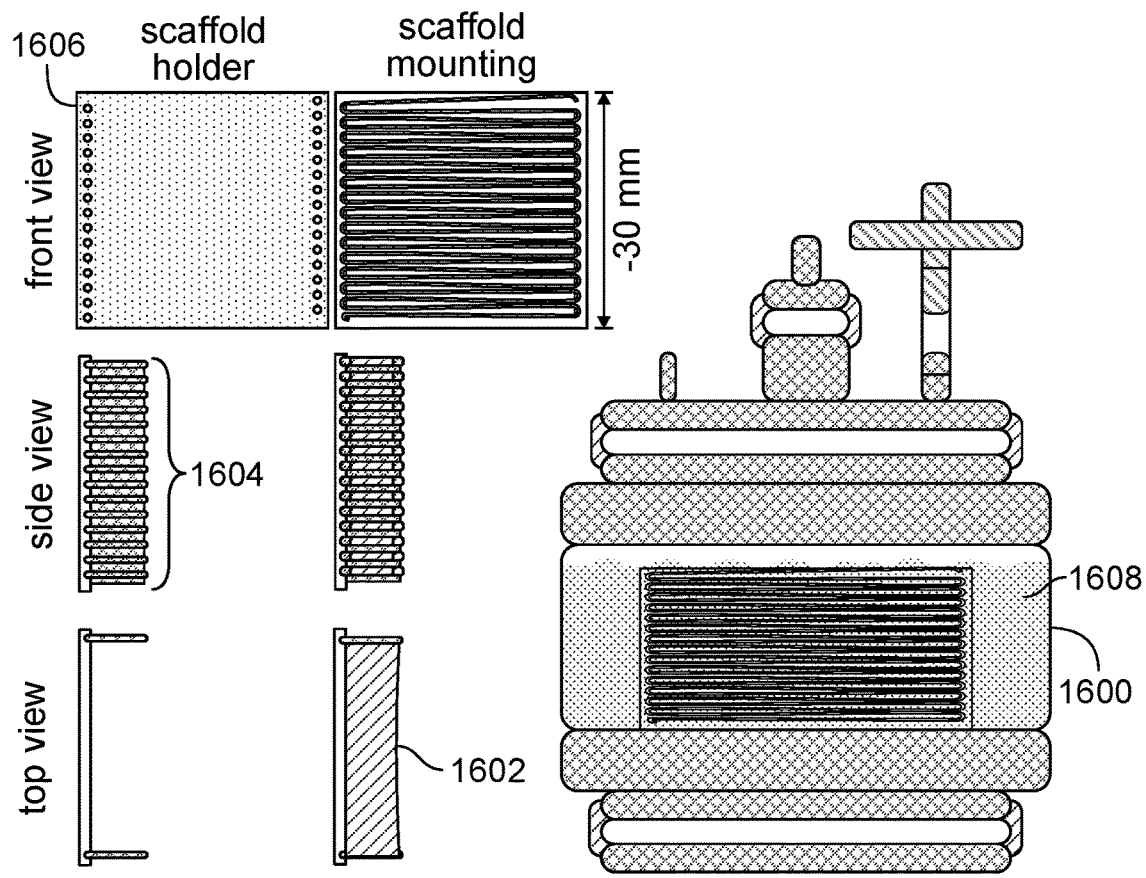
FIG. 16 illustrates an example of a scaffold tray in accordance with some embodiments.

In the example shown, scaffold bioreactor 400 includes a scaffold tray 410 on which scaffold 402 is situated. A bottom portion of scaffold tray 410 includes a plurality of supports, such as support 403, on which scaffold 402 is configured to be seated. The purpose of a scaffold tray, such as scaffold tray 410, is to provide separation between scaffolds and allow media to drain from the scaffold while facilitating oxygenation to all surfaces of the scaffold. In some embodiments, scaffold tray 410 includes a raised mesh-like support where scaffold 402 sits. The mesh allows media to drain from scaffold 402 while allowing the bottom surface to contact ambient air and media rather than being flush with a flat surface of scaffold tray 410. In some embodiments, scaffold 402 is suspended within scaffold tray 410 by being clamped on opposing lateral ends of scaffold tray 410. This format, as seen in FIG. 15, has the added benefit of applying passive tension to scaffold 402, which aids with muscle cell differentiation and cell alignment. Scaffold tray 410 may be customized to support several scaffold formats (e.g., porous sponges, sponges with aligned microtubular pores, hollow fibers, nanofibrous membranes/mats, hydrogels, fibers, thin films, perforated films). In some embodiments, a scaffold tray, as seen in FIG. 16, contains an array of rods. A membrane/film-based scaffold may be woven in-between the rods to (1) provide passive tension, (2) maximize space utilization in the bioreactor, and (3) maintain space between individual layers of the scaffold to enable nutrient and oxygen diffusion. In some embodiments, a scaffold is in sheet-form (as seen in FIG. 3) or rolled form. For a scaffold that is in sheet-form, the scaffold sheet is pre-stretched, then held down on the two ends to apply tension and facilitate fiber alignment in the scaffold. This will help muscle cells to differentiate and orient in their native form.

A fluid, such as growth media or differentiation media, is provided to scaffold 402 via dispensers 406a, 406b, 406c. In the example shown, the fluid has a level 401 within scaffold tray 410. In some embodiments, scaffold tray 410 is reusable. In some embodiments, scaffold tray 410 is a single-use tray. In some embodiments, scaffold tray 410 is part of product package that the consumers bring home. A bottom portion of scaffold tray 410 is perforated (e.g., perforation 408) to allow the circulation of the fluid back to a recirculation media tank via channel 409.

In some embodiments, scaffold tray 410 is constructed from a material (e.g., siliconized glass, electropolished stainless steel) that is anti-adherent to promote cell adhesion to scaffold 402 only and not to scaffold tray 410. In some embodiments, scaffold tray 410 is treated with an anti-adhesion coating to minimize the cell attachment to the tray surface instead of scaffold 402.

FIG. 5 is a diagram illustrating a scaffold bioreactor in accordance with some embodiments. Scaffold bioreactor 500 enables media to be re-used and recirculated during a batch production of cultured meat. This improves nutrient utilization and reduces the amount of waste in the production of cultured meat.

In the example shown, scaffold bioreactor 500 includes a vessel 502 coupled to a media recirculation tank 512 via manifolds 510, 520. The combination of media recirculation tank 512 and manifolds 510, 520 act as a circulatory system for scaffold bioreactor 500. Prior to media fill and culture, the interior of scaffold bioreactor 500 is sterilized via steam or chemical sterilant. Vessel 502 includes a plurality scaffold trays 501a . . . 501n. Each scaffold tray includes a corresponding scaffold. Depending on the scaffold format, scaffolds could be mounted into the trays 501a . . . 501n prior to sterilization and be subject to sterilization simultaneously with vessel 502. In some embodiments, the scaffolds are pre-sterilized by other means and then mounted onto the scaffold trays 501a . . . 501n aseptically after vessel sterilization. Vessel 502 includes an input line 503 and an output line 504. In some embodiments, input line 503 is used to facilitate the aseptic delivery of gasses, such as air, nitrogen, carbon dioxide, and/or oxygen. In some embodiments, output line 504 is used to remove from scaffold bioreactor 500 gas waste products produced by cells included in the scaffold trays 501a . . . 501n, such as dissolved carbon dioxide ($dCO_2$) and ammonia.

Media recirculation tank 512 includes fluid 511 (e.g., cell inoculum, growth media, differentiation media, wash buffers, cleaning solutions), a sparger 513, and one or more sensors 515. Gas (e.g., air, oxygen) is sparged into media recirculation tank 512 via sparger 513 and a metabolic waste produced by cells, such as $dCO_2$, may be removed from media recirculation tank 512 via output line 514.

Scaffold bioreactor 500 includes an input port 530. Input port 520 is used to connect vessel 502 to media recirculation tank 512 via manifold 510. Scaffold bioreactor 500 includes pump 550. Once scaffold bioreactor 500 is ready for culture, pump 550 may be activated to cause fluid 511 (e.g., a concentrated cell suspension) to be provided from media recirculation tank 512 or a separate tank to the trays 501a . . . 501n to submerge the scaffolds via manifold 510. In some embodiments, once scaffold bioreactor 500 is ready for culture, cell-free media is dispensed to pre-hydrate the scaffolds prior to inoculation.

Pump 550 is coupled to controller 552. Controller 552 may be configured to cause fluid 511 to be intermittently provided from media recirculation tank 512 to the scaffold trays 501a . . . 501n. For example, a pump cycle associated with pump 550 may include pump 550 being turned on for 10 seconds and then turned off for 40 seconds. In some embodiments, prior to a batch being started, controller 552 is configured to pre-program pump 550 with a particular pump cycle that is associated with a particular type of meat product. In some embodiments, controller 552 is configured to control pump 550 in real-time. In some embodiments, controller 552 is configured to control pump 550 based on an output of the one or more sensors 515 included in media recirculation tank 512. The one or more sensors 515 may monitor culture conditions including but not limited to temperature, pH, headspace gas composition, dissolved gas composition, tissue density, metabolite concentrations, and/or osmolarity.

Vessel 502 includes an output port 540. Output port 540 is used to connect vessel 502 to media recirculation tank 512 via manifold 520. Fluid 511 may be provided to each of the scaffolds included in scaffold trays 510a . . . 501n via dispensing manifolds 510a . . . 510n, respectively. Fluid may be drained from each of the scaffold trays 510a . . . 510n via return manifolds 520a . . . 520n, respectively and returned to media recirculation tank 512 via manifold 520. The fluid is re-oxygenated by exposure to air when it drains from the scaffold trays 510a . . . 510n, flows in the scaffold trays 510a . . . 510n, and collects in the channels. While in media recirculation tank 512, oxygen gas may be sparged into the fluid to further oxygenate it to a level beyond air saturation. The fluid then may be re-circulated back into vessel 502 by pump 550.

Figure 17:
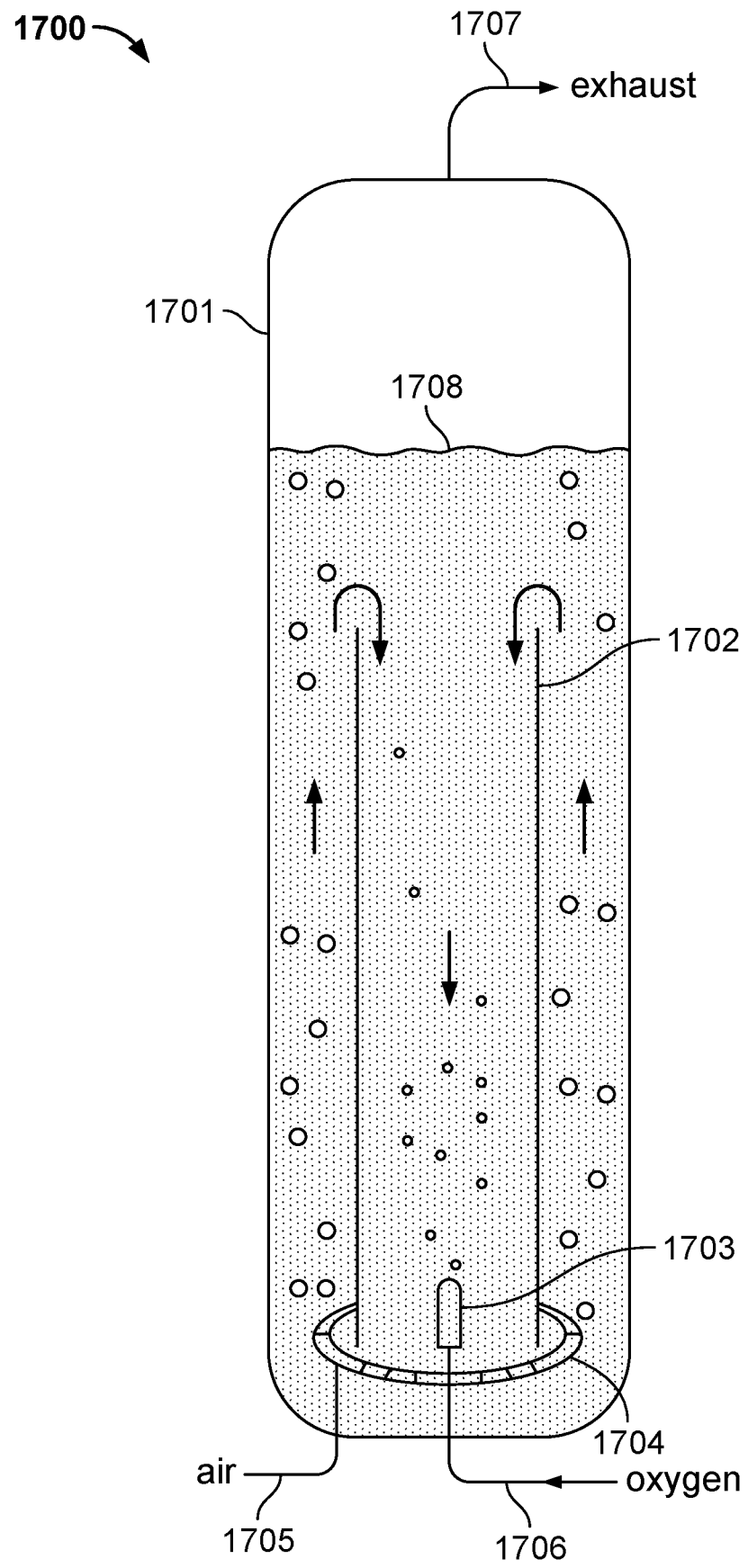
FIG. 17 is a diagram illustrating an airlift bioreactor in accordance with some embodiments.

In some embodiments, media recirculation tank 512 is airlift bioreactor 1700, as seen in FIG. 17, that includes a body 1701, an inner tube 1702 located within the body 1701, a first sparger 1703 configured to sparge oxygen within the inner tube 1703 via an input line 1706, and a second sparger 1704 configured to sparge a mixture of air/nitrogen/carbon dioxide within an annular space between the body 1701 and the inner tube 1702 via a second input line 1705. The two operations are carried out in a functional-closed system within the same aseptic envelope. This approach allows independent control of dissolved oxygen and dissolve carbon dioxide level of the recirculating media. This approach can greatly simplify the process control and eliminate the productivity constraint from the two often competing control objectives. In some embodiments, a mixture of air/nitrogen/carbon dioxide is sparged within the inner tube 1702 and oxygen is sparged within the annular space between the body 1701 and the inner tube 1702.

FIGS. 6A and 6B illustrate an operation of a scaffold bioreactor in accordance with some embodiments. In the example shown, scaffold bioreactor 400 includes a scaffold tray 410 in which a scaffold 402 resides. The scaffolds within a scaffold bioreactor, such as scaffold 402, are kept submerged in cell suspension to allow cells to adhere to the substrate of scaffold 402. After the adhesion period, unadhered cells and excess media are drained from the tray 410 via a plurality of perforations, such as perforation 408, and returned to a media recirculation tank via channel 409.

Fluid 601 (e.g., culture media) is then continuously dispensed, as seen in FIG. 6A, through manifold 404 to deliver nutrients to the tissue culture via dispensers 406a, 406b, 406c. Scaffold 402 is initially kept submerged as cells proliferate. Within the media recirculation tank, fluid 601 (e.g., circulating media) is analyzed for pH, DO, metabolite concentrations, etc. When cells reach high density, the oxygen consumption rate may not be able to be met via circulation of fluid 601 alone, that is, the cells need more oxygen. At this point, as seen in FIG. 6B, the culture can switch into enhanced oxygenation mode by turning off a pump, such as pump 550, in which fluid flow is periodically suspended as the fluid 601 in the scaffold tray 410 drains to expose the scaffold culture to the air temporarily for oxygenation through the thin liquid film 651 remaining on the scaffold surface. The amount of time before the culture is switched into enhanced oxygenation mode may be based on a timer. One or more empirical experiments may be performed on a small scale scaffold to determine the amount of time. The thin liquid film has little resistance to the mass transfer of oxygen, thus boosting the oxygen transfer rate significantly.

Before scaffold 402 loses moisture or nutrients become depleted, media circulation is re-initiated by turning on a pump, such as pump 550, to re-submerge scaffold 402 in fluid 601. The alternating cycles help meet the demand for both the nutrients and oxygen even at high cell density. The cycle time can be optimized to facilitate cell expansion and maturation.

Figure 18:
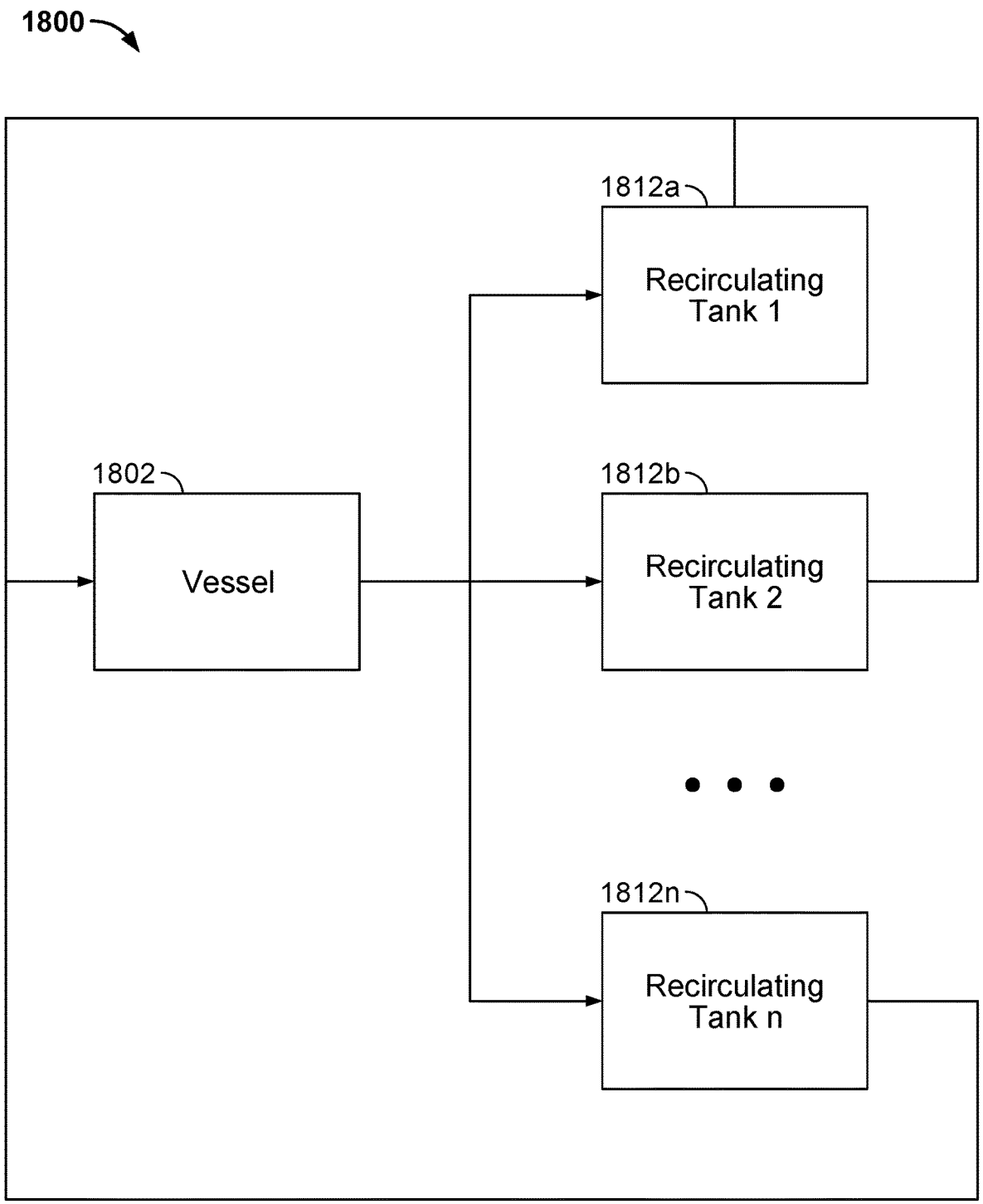
FIG. 18 is a block diagram illustrating a vessel being connected to a plurality of recirculation tanks.

Media can be treated, supplemented, or removed via the media hold/treatment vessel. For example, if differentiation media is required, the growth media can be drained and exchanged with a different formulation. At the end of a batch, scaffold 402 can be rinsed with a conditioning solution to remove excess media components and eliminate the odor of the media, and prepare the meat for market. The media recirculation tank, such as media recirculation tank 512 may be decoupled from the scaffold bioreactor vessel and exchanged with a cleaning tank that includes the conditioning solution. In some embodiments, multiple recirculation tanks can connect to the scaffold bioreactor. The tanks could contain different fluid (e.g., growth media, differentiation media, inoculant, nutrient feed, wash solution, and conditioning solution. A valve manifold could be used to switch from one fluid to another without detaching/reattaching the recirculation tanks. For example, FIG. 18 is a block diagram illustrating a vessel 1802 being connected to recirculation tanks 1812a, 1812b, . . . , 1812n. Although FIG. 18 depicts vessel 1802 being connected to three recirculation tanks, vessel 1802 may be connected to 1:n recirculation tanks.

Subsequently, the scaffold trays are removed from the vessel and may be inserted into plastic pouches, vacuum sealed, and labeled for the market itself. This design eliminates the need for additional post-processing steps and associated equipment, thus greatly reducing the overall production cost.

Figure 7A:
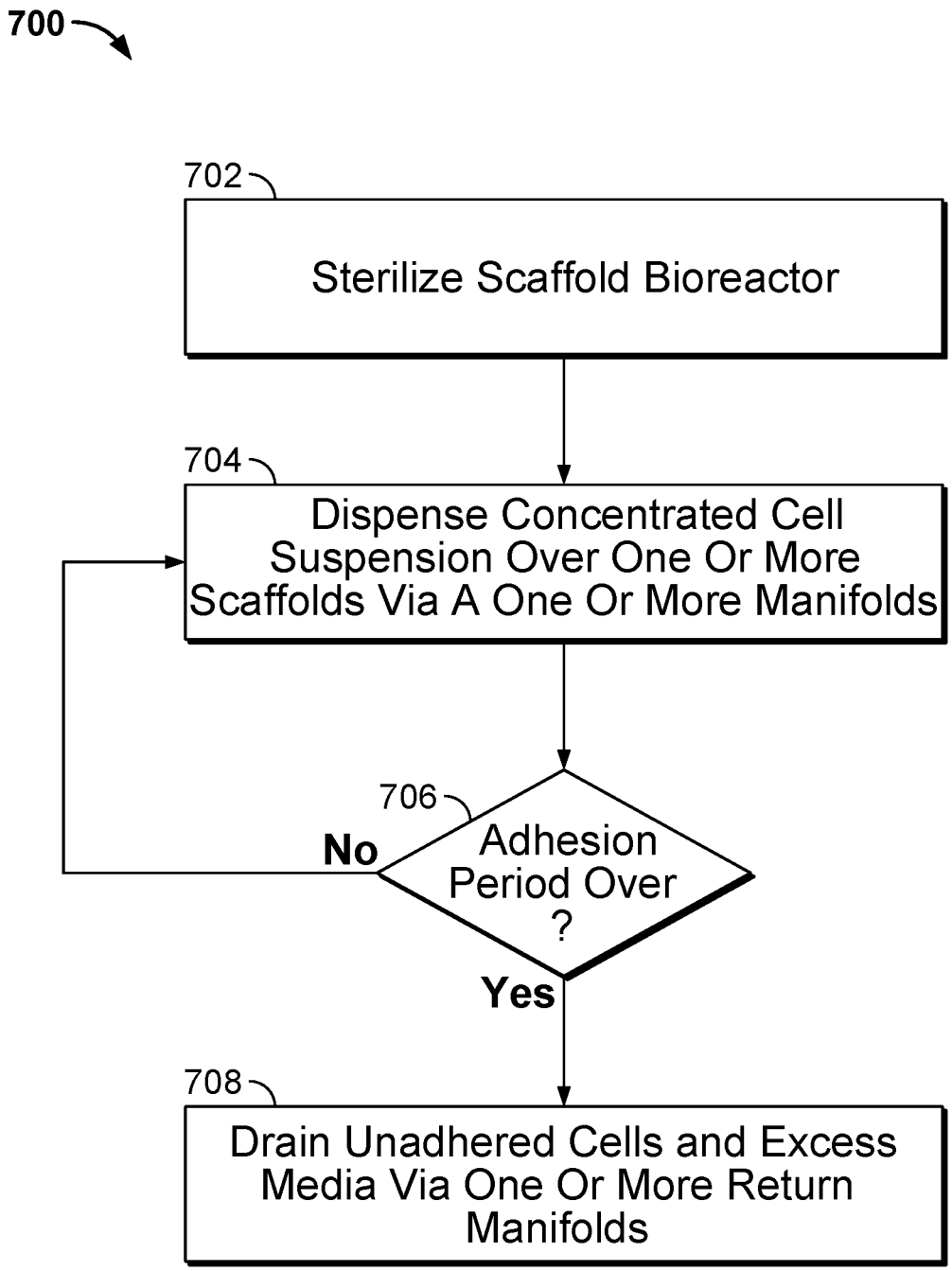
FIG. 7A is a flow diagram illustrating a process for initializing a scaffold bioreactor in accordance with some embodiments.

FIG. 7A is a flow diagram illustrating a process for initializing a scaffold bioreactor in accordance with some embodiments. In the example shown, process 700 may be implemented by a scaffold bioreactor, such as scaffold bioreactor 500.

At 702, the scaffold bioreactor is sterilized. The interior of a scaffold bioreactor may be sterilized with steam or a chemical sterilant. In some embodiments, based on the scaffold format, scaffolds are mounted into trays included in the vessel associated with the scaffold bioreactor prior to sterilization and are subject to sterilization simultaneously with the vessel. In some embodiments, the scaffolds are pre-sterilized by other means and then mounted into the trays aseptically after vessel sterilization.

At 704, a concentrated cell suspension is dispensed over one or more scaffolds included in the scaffold bioreactor via one or more dispensing manifolds. The scaffolds included in the scaffold bioreactor are kept submerged in cell suspension to allow cells to adhere to the substrate of the one or more scaffolds.

At 706, it is determined whether an adhesion period is over. In some embodiments, an adhesion period is a predetermined period of time. In response to a determination that the adhesion period is over, i.e., the predetermined period of time has passed, process 700 proceeds to 706. In response to a determination that the adhesion period is not over, i.e., the predetermined period of time has not passed, process 700 returns to 704.

At 708, unadhered cells and excess media is drained from the one or more scaffold trays that include the one or more scaffolds via one or more return manifolds. The one or more scaffold trays may include one or more perforations that allow the unadhered cells and excess media to be drained from the one or more scaffold trays.

Figure 7B:
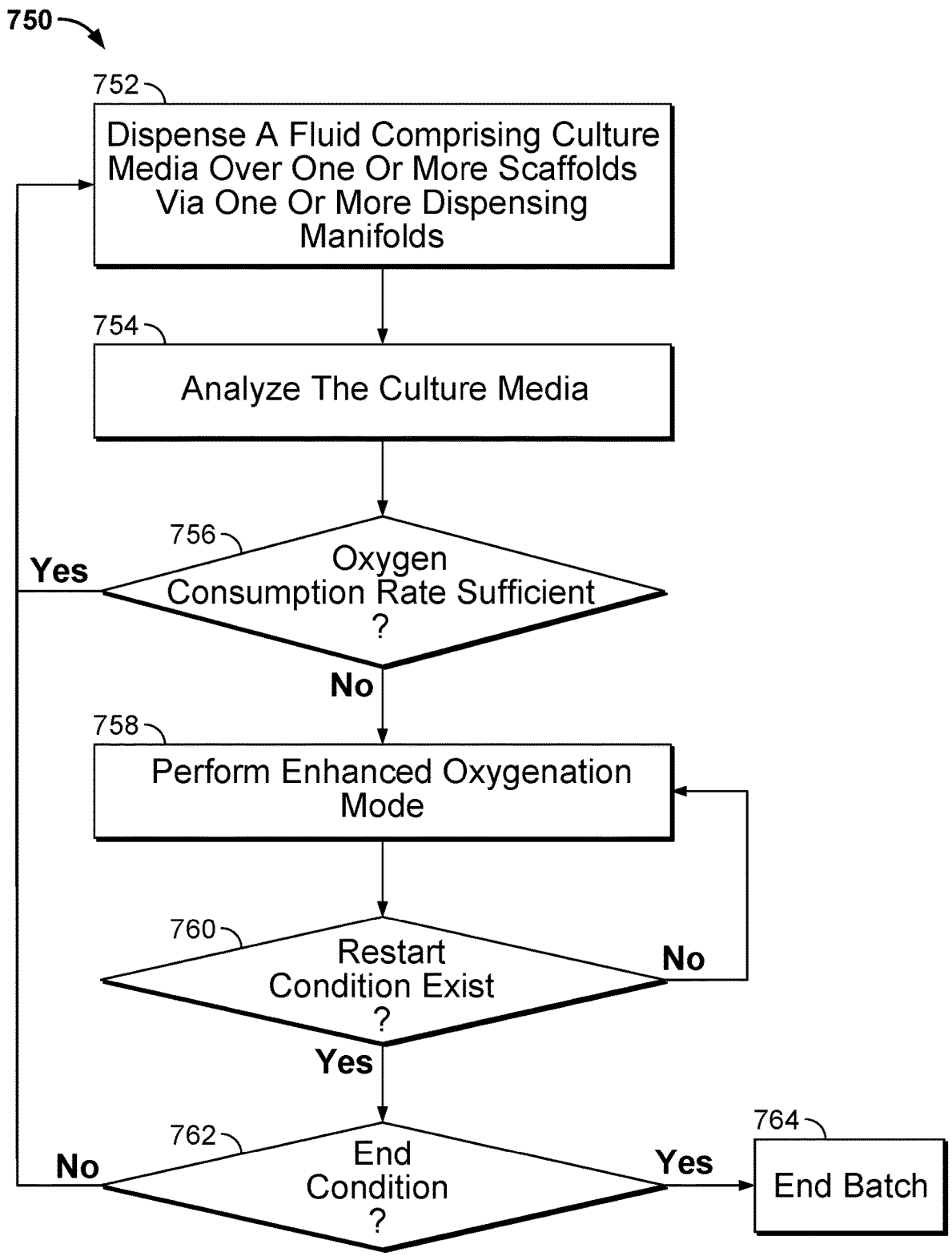
FIG. 7B is a flow diagram illustrating a process for operating a scaffold bioreactor in accordance with some embodiments.

FIG. 7B is a flow diagram illustrating a process for operating a scaffold bioreactor in accordance with some embodiments. In the example shown, process 750 may be implemented by a scaffold bioreactor, such as scaffold bioreactor 500.

At 752, a fluid comprising culture media is dispensed over one or more scaffolds via one or more dispensing manifolds. A pump may cause the culture media to be provided from a media recirculation tank to the one or more scaffolds via the one or more manifolds. The rate at which the culture media is provided (e.g., L/min) may change over time. For example, media circulation may be slow at the beginning of a batch and ramp up as the batch progresses to meet the nutrient demand of proliferating cells. The culture delivers nutrients to the cells to proliferate on the one or more scaffolds. The rate at which the culture media is provided may ramp down during a differentiation phase.

At 754, the culture media is analyzed. The culture media is returned to a media recirculation tank from one or more scaffold trays that include the one or more scaffolds. The media recirculation tank includes one or more sensors. The one or more sensors may monitor culture conditions including but not limited to temperature, pH, headspace gas composition, dissolved gas composition, metabolite concentrations, and/or osmolarity. The culture media may be analyzed for pH, DO, metabolite concentrations, etc. Glucose consumption and/or lactate production rates can be correlated with cell density. A cell density may be determined based on measurements associated with the one or more sensors, such as the metabolite concentration measurements.

At 756, it is determined whether an oxygen consumption rate is sufficient. The cells may reach a threshold density where the oxygen consumption rate may not be able to be met via circulation of the culture media alone, that is, the cells need more oxygen. In response to a determination that the oxygen consumption rate is not sufficient, process 750 proceeds to 758. In response to a determination that the oxygen consumption rate is sufficient, process 750 returns to 752.

At 758, enhanced oxygenation mode is performed. A pump associated with the scaffold bioreactor is turned off. As a result, culture media is no longer dispensed over the one or more scaffolds via the one or more dispensing manifolds. The culture media drains from the one or more scaffold trays that include the one or more scaffolds. This exposes the scaffold culture to the air temporarily for oxygenation through a thin liquid film remaining on a surface of the one or more scaffolds. The thin liquid film has little resistance to the mass transfer of oxygen, thus boosting the oxygen transfer rate significantly.

At 760, it is determined whether a restart pump condition exists. The liquid film remaining on the surface of the one or more scaffolds may dry out or the nutrients included in the liquid film may become depleted. The restart pump condition may be an expiration of a timer. Enhanced oxygenation mode may be carried out for a particular amount of time. An expiration of the timer indicates when enhanced oxygenation mode should no longer be performed. In response to a determination that a restart pump condition exists, process 750 proceeds to 762. In response to a determination that a restart pump condition does not exist, process 750 returns to 758.

At 762, it is determined whether an end condition exists. A batch of cells may be allowed to grow within the scaffold bioreactor for a particular grow period (e.g., seven days). The end condition may exist in the event the batch of cells has been in the scaffold period for the particular grow period. In response to a determination that the end condition exists, process 750 proceeds to 764. In response to a determination that the end condition does not exist, process 750 returns to 752 where the pump associated with the scaffold bioreactor is restarted and culture media is dispensed over the one or more scaffolds via one or more dispensing manifolds.

At 764, the batch is ended. In some embodiments, at the end of the culture, the scaffold is rinsed with a conditioning solution to eliminate the odor of media and prepare the meat for market by switching from the media tank to the conditioning solution tank. After all that, the culture trays may be removed from the chamber and are inserted into plastic pouches, vacuum sealed, and labeled for the market shelf. This will eliminate the need for additional post-processing steps, thus greatly reducing the overall production cost.

Figure 8B:
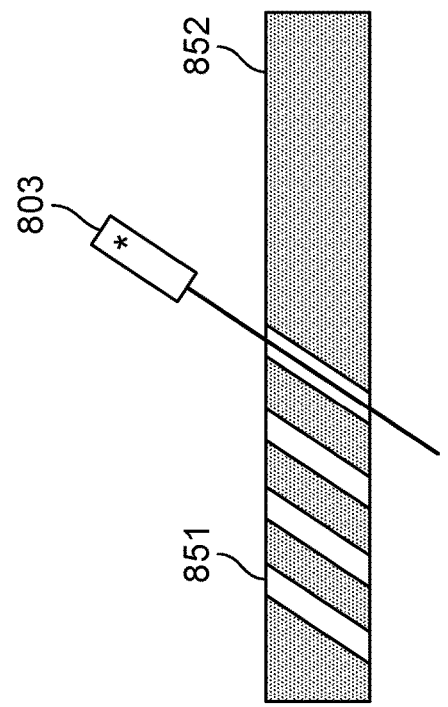
FIGS. 8A and 8B are diagrams illustrating a scaffold in accordance with some embodiments.
Figure 8A:
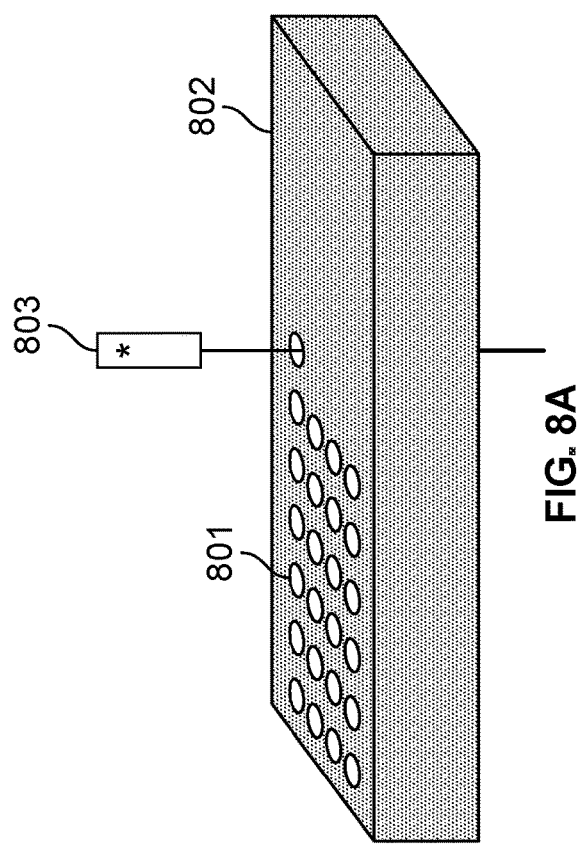

FIGS. 8A and 8B are diagrams illustrating a scaffold in accordance with some embodiments. FIG. 8A illustrates a scaffold 802 that includes a plurality of vertical channels, such as vertical channel 801. FIG. 8B illustrates a scaffold 852 that includes a plurality of angled channels, such as angled channel 851. In some embodiments, scaffolds 802, 852 (e.g., a scaffold sheet or block) may be perforated using laser 803. The plurality of channels (vertical or angled) act as capillary blood vesicles in animal bodies to facilitate nutrients and oxygen penetration deep into the scaffold, that is, increasing the media penetration beyond the surface layer of scaffolds 802, 852.

Figure 9:
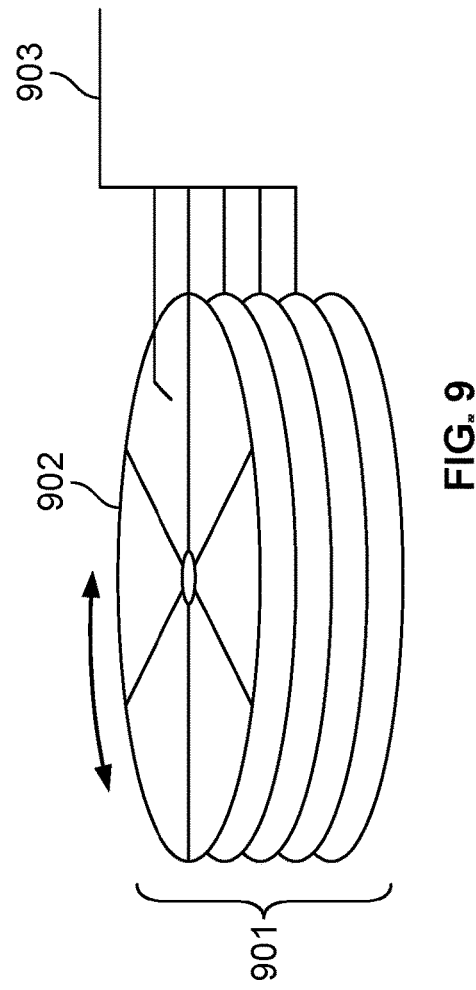
FIG. 9 illustrates a plurality of trays in accordance with some embodiments.

FIG. 9 illustrates a plurality of trays in accordance with some embodiments. In the example shown, the plurality of trays 901 are circular and stacked in a cylindrical pattern. In some embodiments, the plurality of trays 901 are stationary. In some embodiments, the plurality of trays are rotating. Each tray may be associated with a plurality of scaffolds area, such as scaffold area 902. Each tray included in the plurality of trays 901 is associated with a corresponding dispensing manifold that is a branch of central manifold 903.

Figure 10:
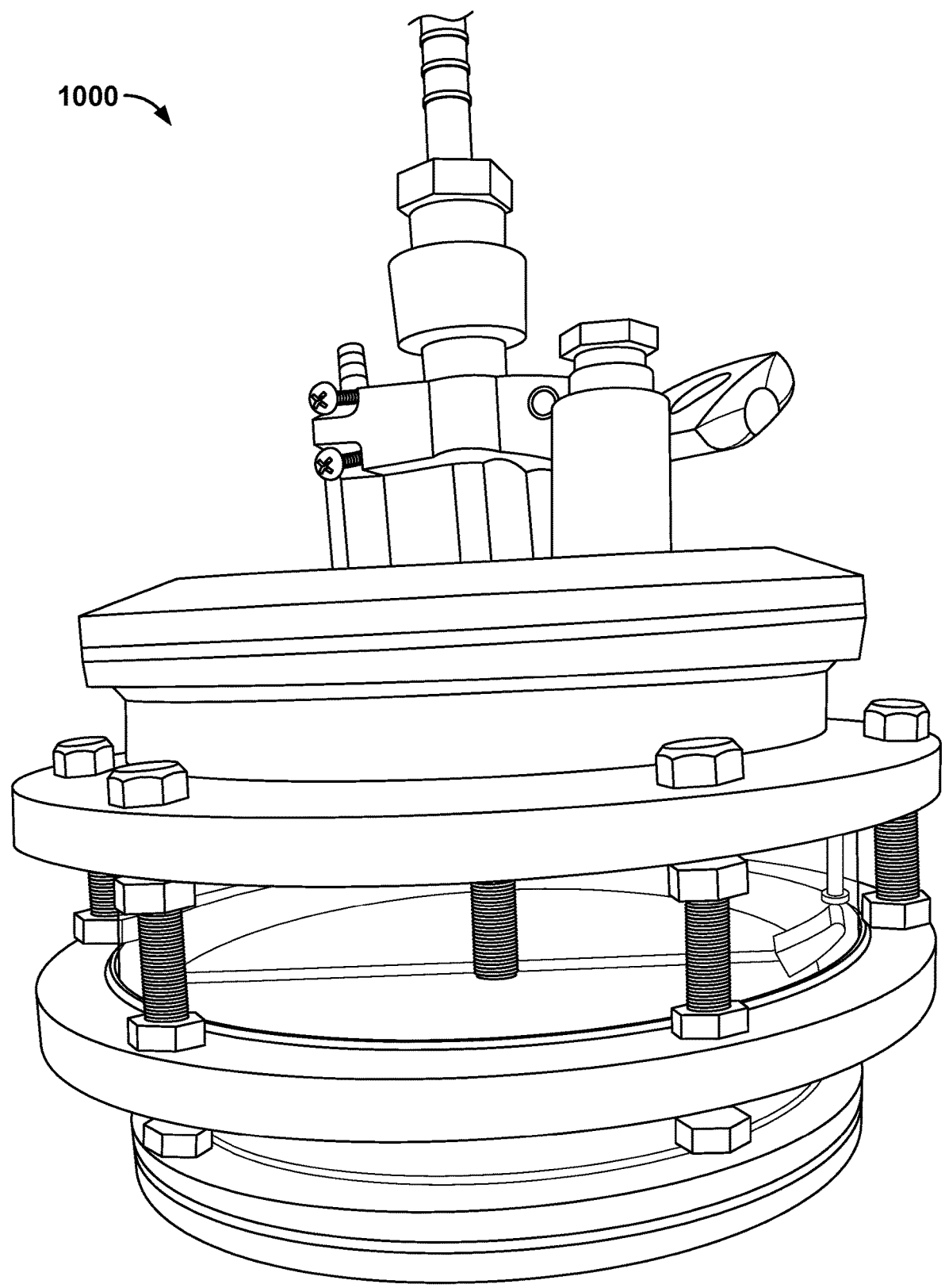
FIG. 10 illustrates an example of a scaffold bioreactor in accordance with some embodiments.

FIG. 10 illustrates an example of a scaffold bioreactor in accordance with some embodiments. In the example shown, scaffold bioreactor 1000 is a prototype that can fit inside a standard cell culture incubator. Scaffold bioreactor 1000 includes a 6" tri-clamp with ports for liquid addition, liquid removal, and gas exchange. The interior of scaffold bioreactor 1000 is configured to hold a scaffold tray.

Figure 11:
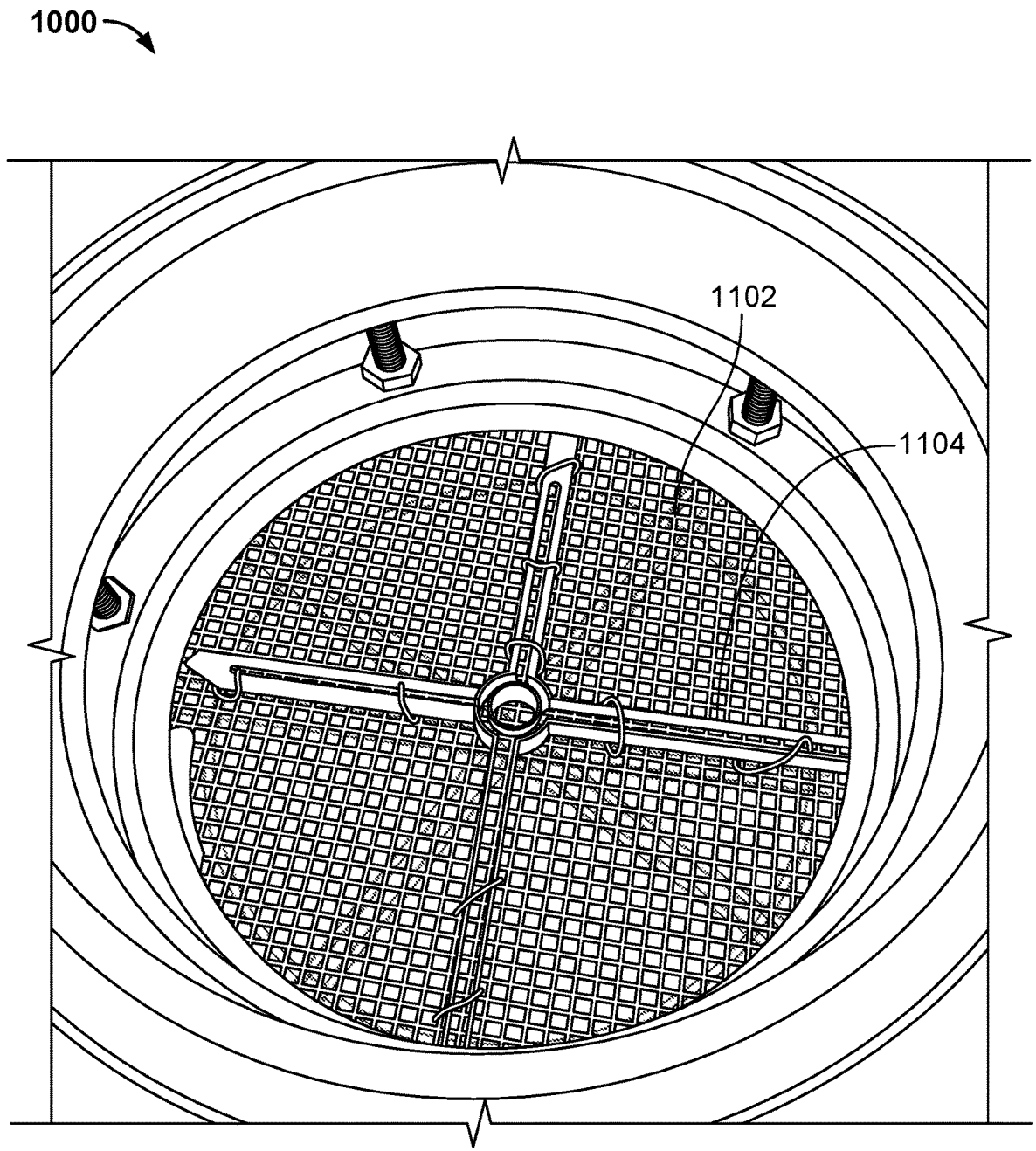
FIG. 11 illustrates an example of a scaffold tray within a scaffold bioreactor prototype in accordance with some embodiments.

FIG. 11 illustrates an example of a scaffold tray within a scaffold bioreactor prototype in accordance with some embodiments. In the example shown, scaffold tray 1102 is located with a scaffold bioreactor prototype 1000 and includes an acrylic support at a bottom of the vessel, a mesh 1102 that sits on top of the support, and a divider 1104 to separate scaffold samples. A dip tube may be inserted in the center of the tray to drain media from the bottom of the vessel.

Figure 12:
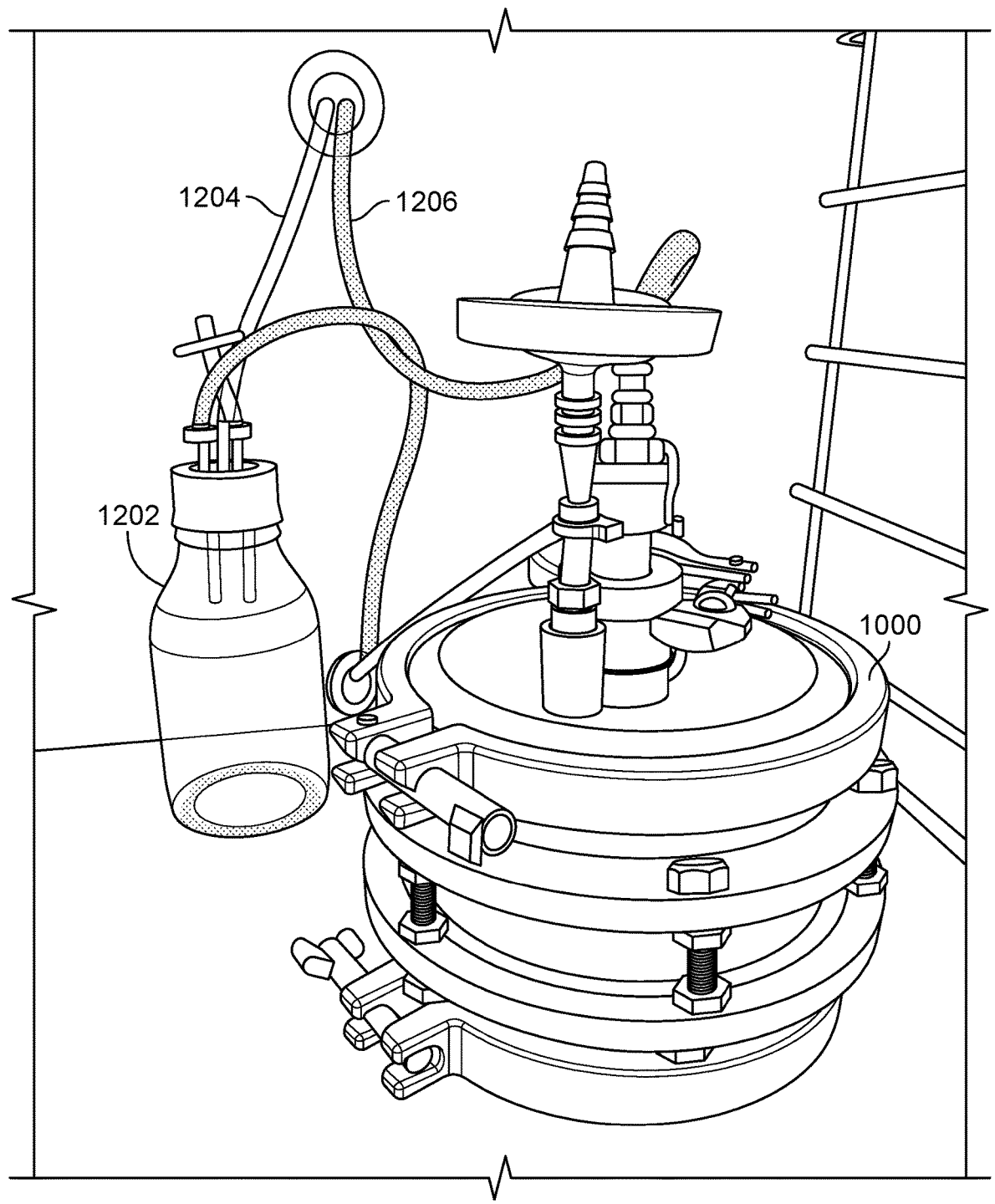
FIG. 12 illustrates an example of a scaffold bioreactor running with a cell culture incubator in accordance with some embodiments.

FIG. 12 illustrates an example of a scaffold bioreactor running with a cell culture incubator in accordance with some embodiments. In the example shown, scaffold bioreactor 1000 is connected to media bottle 1202 via pumpable tubing 1204, 1206 which is coupled with two peristaltic pumps (not shown) to regulate media circulation.

Figure 13:
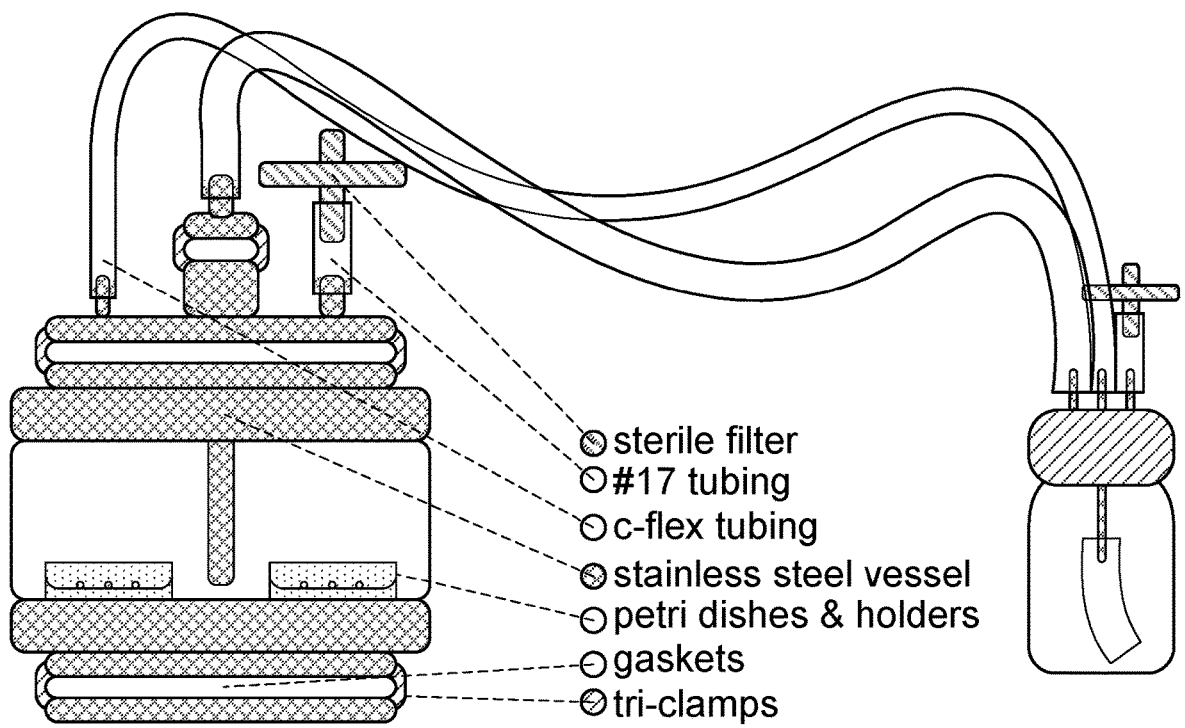
FIG. 13 illustrates a schematic of a scaffold bioreactor prototype assembled pre-sterilization in accordance with some embodiments.
Figure 14:
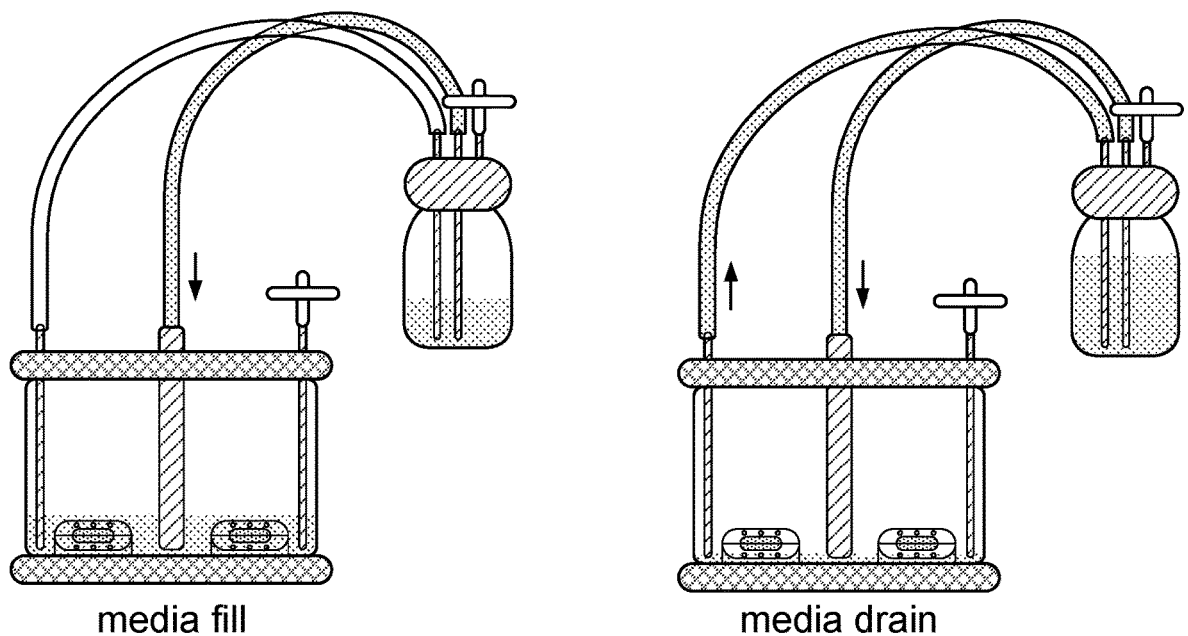
FIG. 14 illustrates a schematic of media circulation within the scaffold bioreactor prototype.

FIG. 13 illustrates a schematic of a scaffold bioreactor prototype assembled pre-sterilization in accordance with some embodiments. FIG. 14 illustrates a schematic of media circulation within the scaffold bioreactor prototype.

FIG. 15 illustrates an example of a scaffold tray in accordance with some embodiments. The scaffold tray 1500 includes a single scaffold or layers of a scaffold 1501 that are held suspended in a perforated scaffold tray by a clamp 1502.

FIG. 16 illustrates an example of a scaffold tray in accordance with some embodiments. A scaffold 1602 is woven between rods 1604 secured on a scaffold tray/holder 1606 to produce a multi-layered system with gaps between layers dictated by the rods 1604. The tray/holder 1606 is placed within the bioreactor chamber 1600. The rods 1604 increase the surface area of the scaffold 1602 in a manner that retains gas between the different layers to enable contact with media, such as media 1608 and contact with air for oxygenation. The rods 1604 may also enable seeding of cells on scaffold 1602 easier.

EXAMPLES

Example 1. Scaffold-Based Chicken Cell Culture in Scaffold Bioreactor

Nanofibrous scaffolds were seeded with chicken fibroblast cells at a density of approximately 7.5E5 viable cells/$cm^2$ in ultra-low attachment petri dishes and incubated for 12 hours at 39 deg. C. and 5% carbon dioxide in a standard cell culture incubator for initial cell attachment. The adhesion efficiency was determined by counting the number of suspended (i.e., non-adhered) cells and found to be ~80% for an inoculation density of approximately 5E5 cells/$cm^2$. The cells were determined to be 95.7% viable after seeding. The cell-laden scaffolds were aseptically loaded into the scaffold bioreactor prototype which was flooded with culture media to fully submerge the scaffold constructs. The bioreactor was installed into a standard cell culture incubator (39 deg. C.; 5% carbon dioxide) and media circulation tubing was coupled to two peristaltic pumps. The media addition pump was programmed to continuously add media to the vessel at a rate of 20 mL/minute. The media draining pump was programmed to drain media at a rate of 40 mL/minute in 7.5 minute cycles for enhanced oxygenation. Samples were collected at the initiation of the culture to determine pH, $pCO_2$, $pO_2$, glucose, and lactate levels. After three days, scaffolds were harvested, stained, and imaged to assess cell viability. Cell viability staining and imaging showed that the vast majority of cells were viable and the cells were densely and evenly distributed throughout the scaffold.

TABLE 1

Partial pressure of oxygen and carbon dioxide in scaffold bioreactor overtime as measured by blood-gas analysis.

| Time (hours) | 0 | 18 | 72 |
|---|---|---|---|
| pCO2 (mmHg) | 16.3 | 39.5 | 31.6 |
| pO2 (mmHg) | 187 | 166 | 148 |

TABLE 2

Metabolic rates over 3 days in culture as measured via metabolite analysis.

| Glucose consumption rate (g/cell/hour) | 1.59E−11 |
|---|---|
| Lactate production rate (g/cell/hour) | 2.38E−11 |

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for culturing cells, comprising:
a bioreactor including a scaffold on which the cells tend to adhere and a tray that supports the scaffold, wherein the tray includes an array of rods and the scaffold is woven in-between the array of rods; and
a circulatory system that intermittently flows fluid over the scaffold, wherein the circulatory system includes:
a media recirculation tank that includes the fluid; and
a pump that causes the fluid to flow from the media recirculation tank to the scaffold, wherein the pump is turned on and turned off during a batch of culturing the cells to enable the fluid to intermittently flow over the scaffold.

2. The system of claim 1, wherein the bioreactor includes one or more other scaffolds.

3. The system of claim 2, wherein the scaffold and the one or more other scaffolds are arranged in a three-dimensional layout.

4. The system of claim 1, wherein the fluid includes cell inoculum, growth media, differentiation media, nutrient feed, wash buffers, cleaning solutions, or storage solutions.

5. The system of claim 1, wherein a bottom of the tray is perforated.

6. The system of claim 1, wherein the tray is composed of a mesh.

7. The system of claim 1, wherein the scaffold is comprised of a porous sponge, a sponge with aligned microtubular pores, hollow fibers, nanofibrous membranes/mats, hydrogels, fibers, thin films, or perforated films.

8. The system of claim 1, wherein the scaffold is configured to rotate inside the bioreactor.

9. The system of claim 1, wherein the scaffold is perforated using a laser to produce a plurality of channels within the scaffold.

10. The system of claim 9, wherein the channels are vertically aligned.

11. The system of claim 9, wherein the channels are angled channels.

12. The system of claim 1, wherein the pump is configured to intermittently cause the fluid to flow from the media recirculation tank to the scaffold via a first manifold, and the circulatory system further includes a second manifold configured to drain the fluid from a bottom of the tray that supports the scaffold.

13. The system of claim 12, wherein the media recirculation tank includes one or more sensors including at least one of a temperature sensor, a pH sensor, a headspace gas composition sensor, a dissolved gas composition sensor, a metabolite concentration sensor, and/or an osmolarity sensor.

14. The system of claim 1, wherein the cells are inoculated onto the scaffold.

15. The system of claim 1, wherein the bioreactor is configured to aseptically deliver one or more gases.

16. The system of claim 15, wherein the one or more gases include air, nitrogen, carbon dioxide, and/or oxygen.

17. The system of claim 1, wherein the system for culturing cells further includes a plurality of different tanks that contain different fluid that are connected to the bioreactor.

* * * * *